United States Patent [19]

Hoek et al.

[11] Patent Number: 4,522,938
[45] Date of Patent: Jun. 11, 1985

[54] PROCESS FOR PREPARING A CATALYST

[75] Inventors: Arend Hoek; Johannes K. Minderhoud; Martin F. M. Post, all of Amsterdam, Netherlands

[73] Assignee: Shell Oil Company, Houston, Tex.

[21] Appl. No.: 554,482

[22] Filed: Nov. 22, 1983

[30] Foreign Application Priority Data

Nov. 22, 1982 [NL] Netherlands ............... 8204527

[51] Int. Cl.³ .................... B01J 21/04; B01J 23/06; B01J 23/26; B01J 23/72
[52] U.S. Cl. .................................... 502/307; 502/342; 518/713
[58] Field of Search ................. 502/307, 342; 518/713

[56] References Cited

U.S. PATENT DOCUMENTS 3,840,478  10/1974  Uda et al. ............................. 502/307
3,850,850  11/1974  Moffatt ................................. 252/465
4,107,089   8/1978  Bondar et al. ....................... 502/307

FOREIGN PATENT DOCUMENTS 1245036  9/1971  United Kingdom .
2109263  6/1983  United Kingdom ............... 502/307

Primary Examiner—W. J. Shine
Attorney, Agent, or Firm—Ronald R. Reper

[57] ABSTRACT

Catalysts for the production of methanol from mixtures of carbon monoxide and hydrogen are prepared by dispersing in water a co-precipitate of zinc and at least one of chromium and aluminum together with a co-precipitate of copper, zinc and optionally at least one of chromium and aluminum, followed by spray drying of the dispersion, and calcining the spray dried material.

8 Claims, No Drawings

PROCESS FOR PREPARING A CATALYST

BACKGROUND OF THE INVENTION

The invention relates to a process for the preparation of a catalyst suitable for use in the conversion of a mixture of carbon monoxide and hydrogen into methanol.

Among the catalysts eligible for use in the preparation on a technical scale of methanol from carbon monoxide and hydrogen, those containing copper, zinc and in addition chromium and/or aluminum are of considerable importance. The preparation of these catalysts usually comprise drying and calcining a co-precipitate obtained by adding a basic reacting substance to an aqueous solution containing salts of all the relevant metals. The catalysts thus prepared have a high selectivity towards methanol; however, both their activity and their stability are insufficient.

On the assumption that by changes in the method of preparing the co-precipitate and/or its upgrading a solution might be found to the abovementioned problem, applicants have carried out an investigation into the preparation of these catalysts. Considering; the unexpectedly favorable results which had been obtained earlier by including a spray drying step in the preparation of catalysts for the conversion of $H_2/CO$ mixtures, it was in the first place investigated whether also in the case of the present catalysts such a step might lead to enhanced performance. Spray drying is a process which has been in use for many years for the preparation of small globular particles from a solid or a mixture of solids. The process is carried out by atomizing a dispersion in water of the material to be spray dried through a nozzle or from a rotating disc into a hot gas. The application of spray drying in the preparation of the present catalysts comprised replacing conventional drying of the aforementioned co-precipitate (which had been prepared by precipitating all the metal components together) by spray drying. This change resulted in a considerable improvement of the stability of the catalysts, which was, however, accompanied with a severe drop in activity. In view of the favorable effect spray drying had on the stability of the catalysts, further investigation was carried out to attempt to achieve improved catalysts by introducing changes in the method of preparing the co-precipitate, while maintaining the spray drying. The change in the preparation of the co-precipitate consisted in the preparation not of a single co-precipitate containing all the metals involved, but of two separate co-precipitates having different compositions. The preparation of the catalyst was carried out by dispersing the two co-precipitates together in water, spray drying the dispersion thus obtained and calcining the spray dried material. Extensive investigation during which dispersions were prepared starting from separate co-precipitates having variable compositions which were dispersed in water in different proportions to one another showed that this technique can yield catalysts having both a very high activity and a very high stability, provided that the composition of each individual co-precipitate as well as the mixing ratio of the co-precipitates in the dispersion meet the following requirements.

1. One co-precipitate (hereinafter referred to as co-precipitate (A) should contain zinc as well as chromium and/or aluminum in such quantities that the Zn/(Cr+Al) atomic ratio is 0.25-4.

2. The other co-precipitate (hereinafter referred to as co-precipitate (B) should contain copper as well as zinc and, if desired, chromium and/or aluminum in such quantities that the Cu/Zn atomic ratio is lower than 10 and the (Cr+Al)/(Cu+Zn) atomic ratio is lower than 2.

3. The two co-precipitates should be dispersed in water together and in such quantities that in the dispersion the atomic ratio of the sum of the metals coming from co-precipitate A to the sum of the metals coming from co-precipitate B is 0.25-3 and the $Cu/(Cu+Zn+Cr+Al)$ atomic ratio is higher than 0.1.

Catalysts which, along with a very high activity, show a very high stability can only be obtained by using two separately prepared co-precipitates and spray drying a dispersion containing the two co-precipitates, if all three above-mentioned requirements are met. Any deviation from one or more of these three requirements will result in catalysts having either low activity or low stability, or a combination thereof.

The importance of including a spray drying step in the present catalyst preparation is made evident by the results of an experiment in which two separately prepared co-precipitates were mixed and the mixture was dried and calcined in the conventional manner. Although the co-precipitates used met the requirements mentioned under (1) and (2) and the mixing ratio used met the requirements mentioned under (3), the catalyst obtained showed moderate activity and extremely low stability.

SUMMARY OF THE INVENTION

The present patent application therefore relates to a process for the preparation of a catalyst, which comprises dispersing in water a co-precipitate A containing zinc as well as chromium and/or aluminum in such quantities that the Zn/(Cr+Al) atomic ratio is 0.25-4, and a co-precipitate B containing copper as well as zinc and, if desired, chromium and/or aluminum in such quantities that the Cu/Zn atomic ratio is lower than 10 and the (Cr+Al)/(Cu+Zn) atomic ratio is lower than 2, and in such quantities that in the water dispersion the atomic ratio of the sum of the metals coming from co-precipitate A to the sum of the metals coming from co-precipitate B is 0.25-3 and the $Cu/(Cu+Zn+Cr+Al)$ atomic ratio is higher than 0.1, followed by spray drying the dispersion thus obtained and then calcining the spray dried material.

The invention further comprises a catalyst prepared according to the invention.

The invention also relates to a process for the preparation of methanol by contacting a feed mixture of carbon monoxide and hydrogen at elevated temperature and pressure with a catalyst prepared according to the invention which catalyst has then undergone a reduction step.

In the process according to the invention two metal-containing co-precipitates are used which have been prepared separately. The preparation of each of these co-precipitates may very suitably be carried out by adding a basic reacting substance to an aqueous solution containing salts of the relevant metals. The basic reacting substance is preferably used in the form of an aqueous solution. Suitable basic reacting substances which may be used in the preparation of the metal-containing co-precipitates are ammonia, soda and alkali metal hydroxides. Co-precipitation is preferably carried out in a mixture with a continuous supply of an aqueous solution containing the relevant metal salts and an aqueous solution of the basic reacting substance in stoichiometric quantities, calculated on the metals and with a continuous discharge of the co-precipitate formed. Before the co-precipitates are together dispersed in water, they should advisably be allowed to age in the mother liquor for some time and subsequently be washed thoroughly with water.

In the process according to the invention a co-precipitate A should be used in which the $Zn/(Cr+Al)$ atomic ratio is in the range of 0.25-4. Preferably a co-precipitate A is chosen in which this atomic ratio is 0.5-3. As regards co-precipitate B in which the Cu/Zn atomic ratio should be lower than 10 and the $(Cr+Al)/(Cu+Zn)$ atomic ratio lower than 2, preference is given to the use of a co-precipitate B in which these atomic ratios are lower than 5 and lower than 1.5, respectively. As regards the mixing ratio of the two co-precipitates, which should be chosen such that in the dispersion the atomic ratio of the sum of the metals coming from co-precipitate A to the sum of the metals coming from co-precipitate B should be 0.25-3 and the $Cu/(Cu+Zn+Cr+Al)$ atomic ratio higher than 0.1, this mixing ratio should preferably be chosen such that said atomic ratios are 0.5-2 and higher than 0.15, respectively.

The catalysts which can be produced according to the invention contain copper and zinc and in addition chromium and/or aluminum. Preference is given to Cu/Zn/Cr and Cu/Zn/Cr/Al catalysts. These catalysts are preferably prepared by using a co-precipitate A which, as the metals, contains exclusively zinc and chromium. For the preparation of Cu/Zn/Cr catalysts the two preparing combinations that are feasible (Zn/Cr+Cu/Zn or Zn/Cr+Cu/Zn/Cr) are in conformity with said preference. For the preparation of Cu/Zn/Cr/Al catalysts, where six preparing combinations are feasible, preference is therefore given to the combinations Zn/Cr+Cu/Zn/Al and Zn/Cr+Cu/Zn/Cr/Al.

The catalysts prepared according to the process of the invention are excellently suitable for use in the conversion of a mixture of carbon monoxide and hydrogen into methanol. The present patent application therefore also relates to a process for the conversion of a mixture of carbon monoxide and hydrogen into methanol using a catalyst obtained according to the invention, starting from two separate co-precipitates A and B and using spray drying. Before they are suitable for this use, the catalysts should be reduced. This reduction is preferably carried out at a temperature of 150°-350° C. The $H_2/CO$ mixture used preferably has a $H_2/CO$ molar ratio higher than 1.0. Examples of suitable $H_2/CO$ mixtures eligible as feeds to be used in the process are $H_2/CO$ mixtures obtained by coal gasification and $H_2/CO$ mixtures obtained in the catalytic steam reforming of light hydrocarbons, such as methane.

The conversion of $H_2/CO$ mixtures into methanol by using a catalyst prepared according to the invention is preferably carried out at a temperature in the range of 175°-350° C. and particularly of 200°-275° C., a pressure in the range of 5-150 bar and particularly of 20-100 bar and a space velocity in the range of 250-25000 Nl synthesis gas per l of catalyst per hour and particularly of 500-10000 Nl synthesis gas per l catalyst per hour. In view of the activity and stability of the catalyst the feed used is preferably a $CO_2$-containing $H_2/CO$ mixture and particularly a $H_2/CO/CO_2$ mixture containing 0.5-25% v $CO_2$, calculated on $H_2/CO/CO_2$ mixture. Usually a synthesis gas prepared by coal gasification or by catalytic steam reforming of light hydrocarbons contains a quantity of $CO_2$ which lies within the limits given hereinbefore. If the available synthesis gas contains too much $CO_2$, the $CO_2$ concentration may be reduced by washing the gas. If the available synthesis gas contains too little $CO_2$, $CO_2$ may be added or the synthesis gas may be subjected to the CO shift reaction $(CO+H_2O \rightleftharpoons CO_2+H_2)$. Irrespective of the $CO_2$ content of the synthesis gas the latter reaction may have to be carried out any way in order to raise the $H_2/CO$ ratio of a synthesis gas with a low $H_2/CO$ ratio.

The conversion of a $H_2/CO$ mixture into methanol by using a catalyst prepared according to the invention may be carried out using a fixed catalyst bed or a moving catalyst bed, and particularly a fluidized catalyst bed. Since the catalysts have very high activity, high degrees of conversion can be achieved at high space velocities. When the catalyst is used in a fixed bed this may produce problems in connection with the heat discharge. Since the problem of heat discharge plays a much less important role when a fluidized catalyst bed is used, the present catalysts are preferably used in the form of a fluidized bed.

The conversion of a $H_2/CO$ mixture into methanol using a catalyst according to the invention may very suitably be carried out as an individual process in which the synthesis gas is converted in a single step. If desired, unconverted synthesis gas may be recirculated.

The conversion of a $H_2/CO$ mixture into methanol using a catalyst prepared according to the invention may also very suitably be carried out as part of a multi-step process for the conversion of a $H_2/CO$ mixture. A number of options may be distinguished in that case, namely:

A. The process is used as the first step of a two-step process in which in the first step methanol is formed and in which $H_2$ and CO present in the reaction product of the first step, together with other components of this reaction product, if desired, is contacted in the second step with a catalyst one or more metal components which have activity for the conversion of a $H_2/CO$ mixture into paraffinic hydrocarbons and have been chosen from the group formed by cobalt, nickel and ruthenium.

B. The process is carried out as the first step of a three-step process in which the first two steps are carried out as stated under (A) and in which in the second step a zirconium, titanium or chromium-promoted cobalt catalyst supported on silica as the carrier is used, which catalyst has been prepared by impregnation and/or kneading. In this process the fact is utilized that a catalytic hydrotreatment can be used to convert the high-boiling part of the product of the second step into middle distillates in a high yield. In the present patent application the term "middle distillates" is used to designate hydrocarbon mixtures whose boiling range corresponds substantially with that of the kerosene and gasoil fractions obtained in the conventional atmospheric distillation of crude mineral oil. Said distillation is used to separate from the crude mineral oil one or more gasoline fractions having a boiling range between 30° and 200° C., one or more kerosene fractions having a boiling range between 140° and 300° C. and one or more gasoil fractions having a boiling range between 180° and 370° C.

The three step process mentioned under (B) comprises carrying out a catalytic hydrotreatment as the third step from the two-step treatment mentioned under (A). The feed chosen for the catalytic hydrotreatment is at least that part of the reaction product of the second step whose boiling point lies above the final boiling point of the heaviest middle distillate desired as end product. The hydrotreatment which is characterized by a very low hydrogen consumption, yields middle distillates with a considerably lower pour point than that of those obtained in the direct Fischer-Tropsch conversion of a $H_2/CO$ mixture. Very suitable catalysts for carrying out the catalytic hydrotreatment are those containing one or more noble metals from Group VIII supported on a carrier and in particular a catalyst containing platinum supported on a carrier 13–15% w of which consists of alumina and the rest of silica.

C. The process is used as the first step of a two-step process in which methanol formed in the first step is catalytically converted in the second step into lower olefins and/or aromatic hydrocarbons. Catalysts very suitable for use in the second step of this process are crystalline metal silicates characterized in that, after one hour's calcination in air at 500° C., they have the following properties:

a. an X-ray powder diffraction pattern in which the strongest lines are the lines mentioned in Table A.

TABLE A

| d(Å) |
| --- |
| 11.1 ± 0.2 |
| 10.0 ± 0.2 |
| 3.84 ± 0.07 |
| 3.72 ± 0.06 | b. in the formula which represents the composition of the silicate expressed in moles of the oxides and in which, in addition to $SiO_2$, one or more oxides of a trivalent metal M chosen from the group formed by aluminum, iron, gallium, rhodium, chromium and scandium occur, the $SiO_2/M_2O_3$ molar ratio is higher than 10.

D. The process is carried out as the first step of a two- or three-step process as described under (A) and (B), respectively and the methanol formed in the first step is converted into lower olefins and/or aromatic hydrocarbons as described under (C).

E. The process is carried out as the first step in a process for preparing methanol and generating power, in which from the reaction product of the first step are separated a fraction containing methanol and a fraction containing unconverted synthesis gas. The latter fraction is combusted and the combustion gas is used for generating power in a gas turbine. The hot exhaust gas of the gas turbine is used in the preparation of high-pressure steam, which is utilized for generating power in a steam turbine. In periods of peak loads the methanol prepared may very suitably be used as additional fuel for generating power in the gas turbine.

The invention is now illustrated with the aid of the following example.

EXAMPLE

Three zinc/chromium co-precipitates (co-precipitates A1–A3) and eight copper/zinc/chromium co-precipitates (co-precipitates B1–B8) were prepared.

The preparation of the zinc/chromium co-precipitates was carried out as follows. Zinc nitrate and chromium nitrate were together dissolved in water and the solution thus obtained, together with a stoichiometric quantity of an aqueous ammonia solution, was pumped with stirring through a mixing unit which was kept at a temperature of 20° C. The ratio of the feed rates was chosen such that the pH, measured at the outlet of the mixing unit, had a value between 7 and 8. The Zn/Cr co-precipitate obtained was collected and allowed to age for one hour with stirring at 20° C. The solid was filtered off and washed with water until the wash water was free from nitrate ions.

The preparation of the copper/zinc/chromium co-precipitates was carried out as follows. Copper nitrate, zinc nitrate and chromium nitrate were together dissolved in water and the solution thus obtained, together with a stoichiometric quantity of an aqueous soda solution, was pumped with stirring through a mixing unit which was kept at a temperature of 60° C. The ratio of the feed rates was chosen such that the pH measured at the outlet of the mixing unit has a value between 6 and 7. The Cu/Zn/Cr co-precipitate obtained was collected and allowed to age for one hour with stirring at 20° C. The solid matter was filtered off and washed with water until the wash water was free from nitrate ions.

Co-precipitates A1–A3 and B1–B8 were used to prepare twelve catalysts (catalysts 1–12). The preparation was carried out as follows.

Catalyst 1

Cu/Zn/Cr co-precipitate B1 was dried at 120° C., the dried material was ground to an average particle size of 0.4 mm and the ground material was calcined for one hour at 300° C.

Catalyst 2

With the aid of a turbo stirrer Cu/Zn/Cr co-precipitate B1 was dispersed in water until the content of dry matter in the dispersion was 15% w. The dispersion thus obtained was spray dried in a countercurrent operation in air with the aid of compressed air. The inlet temperature of the air was 250° C. and the outlet temperature of the air was 120° C. The pressure used was 0.4 bar. The powder obtained, which consisted substantially of globular particles of an average particle size of 50 micron, was pressed, ground to an average particle size of 0.4 mm and calcined for one hour at 300° C.

Catalyst 3

Co-precipitates A1 and B2 were together dispersed in water with the aid of a turbo stirrer. The solid matter was filtered off, washed with water and dried at 120° C. The dried material was ground to an average particle size of 0.4 mm and the ground material was calcined for one hour at 300° C.

Catalysts 4 and 5

Up to and including the spray drying the preparation of these catalysts was carried out in substantially the same manner as that of catalyst 2, with the distinction that in the present case the starting material was a dispersion containing both co-precipitate A1 and co-precipitate B2. The spray dried material was divided into two portions. The one portion was used to prepare catalyst 4 by pressing, grinding to an average particle size of 0.4 mm and calcined for one hour at 300° C. The other portion was calcined for one hour at 300° C. to prepare catalyst 5.

Catalysts 6–12

The preparation of these catalysts was carried out in substantially the same manner as that of catalyst 4. In all the cases the starting material was a dispersion which had been obtained by dispersing two separately prepared co-precipitates together in water and subsequently spray drying the dispersion. The spray dried material was used to prepare catalysts 6–12 by pressing, grinding and calcination. The co-precipitates used in the preparation of catalysts 6–12 were partly chosen from the group formed by A1–A3 and partly from the group formed by B2 and B4–B8.

The atomic ratios of the metals present in the co-precipitates used in the preparation of catalysts 1–12 are given in Table B.

The atomic ratio of the two co-precipitates in each dispersion produced, calculated on the sum of the metals present in each co-precipitate is given in Table C. This table also lists the atomic ratios of the metals present in the ready catalysts (for the catalysts prepared by spray drying this ratio is also the atomic ratio of the metals present in the dispersions to be spray dried).

In order to give some more understanding of the data listed in Table C, the preparation of catalyst 4 will hereinafter be pursued somewhat further. This catalyst was prepared starting from co-precipitate A1 having a Zn/Cr atomic ratio of 2:1 and a co-precipitate B2 having a Cu/Zn/Cr atomic ratio of 5:3:2. The two co-precipitates were together dispersed in water in an atomic ratio of 1:1, calculated on the sum of the metals present in each co-precipiate, viz. in addition to a quantity of co-precipitate containing 2/3 gram atom Zn + 1/3 gram atom Cr a quantity of co-precipitate B containing 5/10 gram atom Cu + 3/10 gram atom Zn + 2/10 gram atom Cr was dispersed in water. The dispersion thus prepared therefore contained the metals Cu, Zn and Cr in the atomic ratio $$\frac{5}{10} : \left(\frac{2}{3} + \frac{3}{10}\right) : \left(\frac{1}{3} + \frac{2}{10}\right) =$$

$$\frac{15}{30} : \frac{29}{30} : \frac{16}{30} = 25:48:27$$

TABLE B

| Co-precipitate No. | Atomic ratio of the metals present in the co-precipitate | | |
|---|---|---|---|
| | Cu | Zn | Cr |
| A1 | — | 2 | 1 |
| A2 | — | 6 | 1 |

TABLE B-continued

| Co-precipitate No. | Atomic ratio of the metals present in the co-precipitate | | |
|---|---|---|---|
| | Cu | Zn | Cr |
| A3 | — | 1 | 5 |
| B1 | 25 | 48 | 27 |
| B2 | 5 | 3 | 2 |
| B3 | 2 | 9 | 6 |
| B4 | 2 | 3 | 2 |
| B5 | 15 | 3 | 2 |
| B6 | 5 | 1 | 4 |
| B7 | 25 | 1 | 24 |
| B8 | 3 | 1 | 11 |

TABLE C

| Catalyst No. | Atomic ratio of the metals present in the catalysts | | | Atomic ratio of the co-precipitates in the dispersions produced, calculated on the sum of the metals present in each co-precipitate | |
|---|---|---|---|---|---|
| | Cu | Zn | Cr | | |
| 1 | 25 | 48 | 27 | — | — |
| 2 | 25 | 48 | 27 | — | — |
| 3 | 25 | 48 | 27 | 1 A 1 | 1 B 2 |
| 4 | 25 | 48 | 27 | 1 A 1 | 1 B 2 |
| 5 | 25 | 48 | 27 | 1 A 1 | 1 B 2 |
| 6 | 6 | 60 | 34 | 1 A 1 | 1 B 3 |
| 7 | 24 | 47 | 29 | 1 A 1 | 5 B 4 |
| 8 | 17 | 55 | 28 | 3.5 A 1 | 1 B 5 |
| 9 | 25 | 48 | 27 | 1 A 2 | 1 B 6 |
| 10 | 25 | 23 | 52 | 1 A 3 | 1 B 2 |
| 11 | 25 | 34 | 41 | 1 A 1 | 1 B 7 |
| 12 | 15 | 22 | 63 | 1 A 1 | 3 B 8 |

After reduction in hydrogen at 220° C. catalysts 1–12 were tested for the preparation of methanol from synthesis gas. The testing of catalysts 1–4 and 6–12 was carried out in a 50-ml reactor containing a fixed catalyst bed of 5 ml volume. In eleven experiments (Experiments 1–11) a $H_2/CO/CO_2$ mixture of a volume ratio of 67:31.5:1.5 was passed over each one of catalysts 1–4 and 6–12 at a temperature of 250° C., a pressure of 60 bar and a space velocity of 5000 $Nl\cdot l^{-1}\cdot H^{-1}$. The results of these experiments are given in Table D.

TABLE D

| Exp. No. | Catalyst No. | Yield, kg methanol·(l catalyst)$^{-1}$·h$^{-1}$ | Deactivation, % $\left(\frac{\text{decrease of yield over 100 h}}{\text{average yield over same period}} \times 100\right)$ |
|---|---|---|---|
| 1 | 1 | 0.82 | 5 |
| 2 | 2 | 0.35 | 2 |
| 3 | 3 | 0.74 | 8 |
| 4 | 4 | 0.98 | <1 |
| 5 | 6 | 0.31 | <1 |
| 6 | 7 | 0.45 | 2 |
| 7 | 8 | 0.47 | 4 |
| 8 | 9 | 0.84 | 2 |
| 9 | 10 | 0.92 | 5 |
| 10 | 11 | 0.56 | 7 |
| 11 | 12 | 0.40 | 3 |

Catalyst 5 was tested in a vertically disposed fluidized bed reactor of 175 cm in height and of 500 ml volume containing 150 ml catalyst. In five experiments (Experiments 12–16) $H_2/CO/CO_2$ mixtures were contacted with catalyst 5 at various temperatures, pressures and space velocities. The conditions under which these experiments were carried out are given in Table E. In all the experiments deactivation was less than 1%. The synethesis gas conversions and methanol yields obtained in each of the experiments are also given in Table E.

TABLE E

| Exp. No. | Composition of $H_2/CO/CO_2$ feed | Space velocity $Nl.l^{-1}.h^{-1}$ | Pressure bar | Temperature °C. | Runhour | Conversion of synthesis gas % v | Yield, kg methanol.(l catalyst)$^{-1}.h^{-1}$ |
|---|---|---|---|---|---|---|---|
| 12 | 80:19:1.0 | 4150 | 60 | 250 | 100 | 37 | 0.76 |
| 13 | 67:32:1.2 | 3360 | 60 | 250 | 130 | 48 | 0.73 |
| 14 | 67:32:1.2 | 3360 | 80 | 250 | 150 | 60 | 0.90 |
| 15 | 67:32:1.3 | 1200 | 30 | 230 | 190 | 36 | 0.19 |
|    |           |      |    |     | 786 | 35 | 0.19 |
| 16 | 67:32:1.2 | 3360 | 60 | 250 | 800 | 46 | 0.69 |
|    |           |      |    |     | 1000 | 46 | 0.69 |

On the data given in Tables B–E the following may be remarked. Of catalysts 1–12 mentioned in Table C only catalysts 4 and 5 have been prepared according to the invention. They were obtained starting from two separately prepared co-precipitates and using the method of spray drying. The other catalysts fall outside the scope of the invention. They have been included in the patent application for comparison. Catalyst 1 was prepared starting from a single co-precipitate and without the use of spray drying. Catalyst 2 was prepared starting from a single co-precipitate. Catalyst 3 was prepared without spray drying. Although catalysts 6–12 were obtained starting from two separately prepared co-precipitates A and B and with spray drying being used, they did not meet the criteria of the process according to the invention, since in the case of catalyst 6 the Cu/(Cu+Zn+Cr) atomic ratio in the dispersion was 0.06, in the case of catalysts 7 and 8 the atomic ratio in the dispersion of the sum of the metals coming from co-precipitate A to the sum of the metals coming from co-precipitate B was 0.2 and 3.5, respectively, in the case of catalysts 9 and 10 the Zn/Cr atomic ratio in co-precipitate A was 6 and 0.2, respectively, in the case of catalyst 11 the Cu/Zn atomic ratio in co-precipitate B was 25 and in the case of catalyst 12 the Cr/(Cu+Zn) atomic ratio in co-precipitate B was 2.75.

Of Experiments 1–11 listed in Table D only Experiment 4 was carried out using a catalyst prepared according to the invention. The other experiments have been included in the patent application for comparison. As seen from the results given in Table D, only the catalyst prepared according to the invention displays a combination of very high activity (high yield) and very good stability (very little deactivation).

Experiments 12–16 given in Table E were all carried out using a catalyst which had been prepared according to the invention. As seen from the results given in Table E, the catalysts prepared according to the invention are also very suitable for use in a fluidized bed operation.

We claim:

1. A process for the preparation of a catalyst, which comprises dispersing in water a co-precipitate A comprising zinc as well as chromium and/or aluminum in such quantities that the Zn/(Cr+Al) atomic ratio is 0.25–4 and a co-precipitate B comprising copper as well as zinc and, if desired, chromium and/or aluminum in such quantities that the Cu/Zn atomic ratio is lower than 10 and the (Cr+Al)/(Cu+Zn) atomic ratio is lower than 2, and in such quantities that in the water dispersion the atomic ratio of the sum of the metals coming from co-precipitate A to the sum of the metals coming from co-precipitate B is 0.25–3 and the Cu/(Cu+Zn+Cr+Al) atomic ratio is more than 0.1, followed by spray drying the dispersion thus obtained, and then calcining the spray dried material.

2. A process as in claim 1, wherein a co-precipitate A is used in which the Zn/(Cr+Al) atomic ratio is 0.5–3.

3. A process as in claim 1, wherein a co-precipitate B is used in which the Cu/Zn atomic ratio is lower than 5.

4. A process as in claim 1, wherein a co-precipitate B is used in which the (Cr+Al)/(Cu+Zn) atomic ratio is lower than 1.5.

5. A process as in claim 1, wherein the mixing ratio of the two co-precipitates is such that in the dispersion the atomic ratio of the sum of the metals coming from co-precipitate A to the sum of the metals coming from co-precipitate B is 0.5–2.

6. A process as in claim 1, wherein the mixing ratio of the two co-precipitates is such that in the dispersion the Cu/(Cu+Zn+Cr+Al) atomic ratio is higher than 0.15.

7. A process as in claim 1, wherein the catalyst comprises a metal combination selected from the group consisting of Cu/Zn/Cr and Cu/Zn/Cr/Al.

8. A process as in claim 1, wherein a co-precipitate A is used which contains as metals exclusively zinc and chromium.

* * * * *